United States Patent
Lee et al.

(10) Patent No.: US 11,395,829 B2
(45) Date of Patent: Jul. 26, 2022

(54) INHIBITORS OF METALLO-BETA-LACTAMASES PRODUCED BY MULTIDRUG-RESISTANT BACTERIA

(71) Applicant: MYONGJI UNIVERSITY INDUSTRY AND ACADEMIA COOPERATION FOUNDATION, Gyeonggi-do (KR)

(72) Inventors: Sang Hee Lee, Gyeonggi-do (KR); Jung Hun Lee, Gyeonggi-do (KR); Jeong Ho Jeon, Incheon (KR)

(73) Assignee: MYONGJI UNIVERSITY INDUSTRY AND ACADEMIA COOPERATION FOUNDATION, Gyeonggi-Do (KR)

(*) Notice: Subject to any disclaimer, the term of this patent is extended or adjusted under 35 U.S.C. 154(b) by 0 days.

(21) Appl. No.: 16/690,298

(22) Filed: Nov. 21, 2019

(65) Prior Publication Data

US 2021/0154216 A1    May 27, 2021

(51) Int. Cl.
| | | |
|---|---|---|
| *A61K 31/69* | (2006.01) | |
| *C07F 5/02* | (2006.01) | |
| *A61P 31/04* | (2006.01) | |
| *A61K 45/06* | (2006.01) | |

(52) U.S. Cl.
CPC .............. *A61K 31/69* (2013.01); *A61K 45/06* (2013.01); *A61P 31/04* (2018.01); *C07F 5/02* (2013.01)

(58) Field of Classification Search
USPC ........................................................... 514/64
See application file for complete search history.

(56) References Cited

U.S. PATENT DOCUMENTS

2012/0141384 A1* 6/2012 Tamarkin ................ A61P 31/04
424/45

OTHER PUBLICATIONS

Thornber, Chem. Soc. Rev., 1979, 563-580.*

\* cited by examiner

*Primary Examiner* — Ana Z Muresan
(74) *Attorney, Agent, or Firm* — The PL Law Group, PLLC

(57) ABSTRACT

A compound having Formula I or its derivative may inhibit metallo-beta-lactamases. An investigation studying the effects of the compounds was provided by the invention of the activities of all subclasses (B1, B2, and B3) metallo-beta-lactamases. The compounds can be used for a pharmaceutical product with the ability to restore an anti-bacterial activity of a beta-lactam antibiotic, thereby treating and preventing a bacterial infection in an animal or human subject.

5 Claims, 8 Drawing Sheets

Specification includes a Sequence Listing.

¹H-NMR spectra (ACP-DCPBA)

¹H-NMR spectra (CHP-DCPBA)

$^{13}$C-NMR spectra (CHP-DCPBA)

INHIBITORS OF METALLO-BETA-LACTAMASES PRODUCED BY MULTIDRUG-RESISTANT BACTERIA

FIELD OF THE INVENTION

The invention relates to compounds for use in the inhibition of all subclasses (B1, B2, and B3) metallo-beta-lactamases (MBLs).

BACKGROUND

Beta-lactam antibiotics are one of the most successful drugs used for the treatment of bacterial infections and represent roughly 65% of the total world market for antibiotics (Worthington, et al., *J. Org. Chem.*, 78, 4207 (2013)). Therefore, resistance to beta-lactam antibiotics is one of the most serious problems associated with Gram-negative bacterial infections (Lee, et al., *Lancet Infect. Dis.*, 16, 17-18 (2016)).

Beta-lactamases are bacterial enzymes that hydrolytically inactivate beta-lactams (beta-lactam antibiotics) and are a major cause of the emergence of pathogenic bacteria resistant to beta-lactams such as penicillins, cephalosporins, monobactams, and carbapenems that are a class of highly effective antibiotic agents commonly used for the treatment of severe or high-risk bacterial infections.

Beta-lactamases are produced by various bacteria conferring them resistant to beta-lactam antibiotics such as penicillins, cephalosporins, monobactams, and/or carbapenems (the last resort drugs for treating bacterial infections) (McKenna, Nature, 499, 394-396 (2013); Papp-Wallace, et al., *Antimicrob. Agents Chemother.*, 55, 4943-4960 (2011)). The production of beta-lactamases, a group of enzymes that confer antibiotic resistance in Gram-negative bacteria, is now one of the major barriers in treating Gram-negative infections (Lee, et al., *Lancet Infect. Dis.*, 16, 17-18 (2016); Papp-Wallace, et al., *Antimicrob. Agents Chemother.*, 55, 4943-4960 (2011); Tucker, et al., Cell, 172, 618 (2018)). Beta-lactamases are classified according to their catalytic mechanisms into serine beta-lactamases (classes A, C, and D) and metallo-beta-lactamases (MBLs, class B enzymes further divided into three subclasses B1-B3) (Bush, et al., *Antimicrob. Agents Chemother.*, 54, 969-976 (2010); Galleni, et al., *Antimicrob. Agents Chemother.*, 45, 660-663 (2001)).

MBLs require zinc for catalysis. They have a broad substrate spectrum and can catalyze the hydrolysis of virtually all beta-lactam antibiotics including carbapenems except for monobactams (Palzkill, *Ann. N. Y. Acad. Sci.*, 1277, 91-104 (2013)). The most common families of acquired subclass B1 MBLs identified in Enterobacteriaceae include the VIM-type (Verona integron-encoded metallo-beta-lactamase) and IMP-type (imipenem-resistant *Pseudomonas*) groups, together with the emerging NDM-type (New Delhi metallo-beta-lactamase) group (Nordmann, et al., *Trends Microbiol.*, 19, 588-595 (2011); Walsh, et al., *Clin. Microbiol. Rev.*, 18, 306-325 (2005); Yong, et al., *Antimicrob. Agents Chemother.*, 53, 5046-5054 (2009)). One of the most clinically significant carbapenemases, NDM-1, was first detected in 2008 in *Klebsiella pneumoniae* and *Escherichia coli* in a patient returning to Sweden from India and has been subsequently shown to be present in bacterial isolates in a number of countries worldwide (Yong, et al., *Antimicrob. Agents Chemother.*, 53, 5046-5054 (2009)). IMP-1 was found in a *Serratia marcescens* isolate in Japan in 1991 (Ito, et al., *Antimicrob. Agents Chemother.*, 39, 824-829 (1995)). VIM-1 was first identified in Italy in 1997 (Cornaglia, et al., *Clin. Infect. Dis.*, 31, 1119-1125 (2000); Lauretti, et al., *Antimicrob. Agents Chemother.*, 43, 1584-1590 (1999)), and VIM-2 was then reported in France in a *Pseudomonas aeruginosa* isolate dating from 1996 (Poirel, et al., *Antimicrob. Agents Chemother.*, 44, 891-897 (2000)). GIM-1 (German imi penemase-1: subclass B1 MBL) was first identified in clinical *P. aeruginosa* isolates from Germany in 2002 (Castanheira, et al. *Antimicrob. Agents Chemother.*, 48, 4654-4661 (2004)), and it has also been reported in different clones of multidrug-resistant *P. aeruginosa* isolates from Germany (Rieber H, et al. *J. Antimicrob. Chemother.*, 67, 1043-1045 (2012)). CphA-type (Carbapenemase hydrolyzing *Aeromonas*: subclass B2 MBL) was identified from *Aeromonas hydrophila* (Massidda, et al., *J. Bacteriol.*, 173, 4611-4617 (1991)). Subclass B3 GOB-type MBLs include various allelic variants, all of them expressed by *Elizabethkingia meningoseptica*, a pathogen responsible for neonatal meningitis and opportunistic infections in immunocompromised patients (Bloch, et al., Medicine (Baltimore), 76, 30-41 (1997); Lee, et al., *J. Chin. Med. Assoc.*, 71, 473-476 (2008); Shinha, et al., *IDCases*, 2, 13215 (2015)). GOB-1 (named for class B beta-lactamase of *Chryseobacterium meningosepticum*) was found in a *C. meningosepticum* that is the most clinically important human pathogen (Bellais et al., *Antimicrob. Agents Chemother.*, 44, 1878-1886 (2000)).

Avibactam (formerly NXL104) is a diazabicyclooctane (DBO, non-lactam class) derivative antibiotic, and ceftazidime-avibactam was approved by the FDA in 2015. Avibactam has very good potency in reversibly inhibiting serine beta-lactamase enzymes including Ambler class A (mainly extended-spectrum beta-lactamases (ESBLs) and *Klebsiella pneumonia* carbapenemases (KPCs)), class C, and partial class D (including OXA-1, OXA-10, and OXA-48 subgroup) (Lomovskaya, et al., *Antimicrob. Agents Chemother.*, 61, pii:e01443-17 (2017)). Besides, relebactam (formerly MK-7655A) was developed by another DBO class drug and FDA recently announced the approval of a combination antibiotic, imipenem-cilastatin/relebactam in 2019. Vaborbactam (formerly RPX7009), a cyclic boronate non-beta-lactam agent (structurally distinct from avibactam and relebactam), is beta-lactamase inhibitor and meropenem-vaborbactam was approved by the FDA in 2017. Both inhibitors (relebactam and vaborbacta) display activity against Ambler class A (including ESBLs and KPCs) and class C beta-lactamases (AmpCs).

However, they have not been proven to inhibit class B MBLs (e.g. NDM-, IMP-, and VIM-types) (Zhanel, et al., *Drugs*, 78, 65 (2018)). Also, MBLs are not inhibited by mechanism-based inhibitors such as clavulanate, sulbactam, and tazobactam.

Therefore, there is an imperative need to develop novel MBL inhibitors with broad-spectrum functionality to inhibit all subclasses (B1, B2, and B3) MBLs.

SUMMARY

The invention provides non-beta-lactam inhibitors of metallo-beta-lactamases.

According to an aspect of the present invention, a compound having Formula I or a derivative thereof:

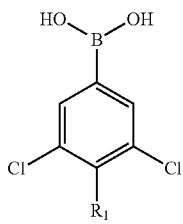

Formula I wherein $R_1$ is H,

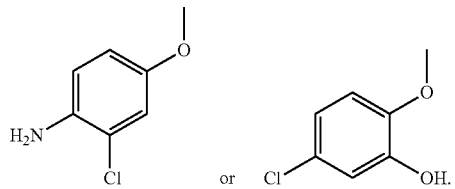

According to an aspect of the present invention, the compound is

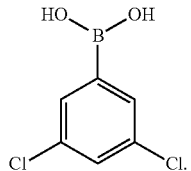 [SMILES: OB(O)c1cc(Cl)cc(Cl)c1]

According to an aspect of the present invention, the compound is

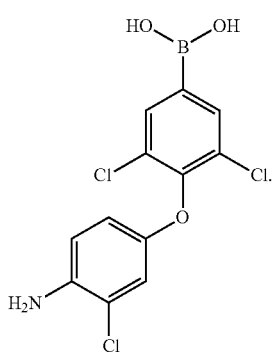 [SMILES: Nc1ccc(Oc2c(Cl)cc(B(O)O)cc2Cl)cc1Cl]

According to an aspect of the present invention, the compound is

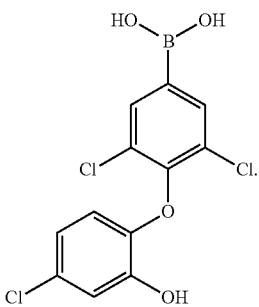 [SMILES: OB(O)c1cc(Cl)c(Oc2ccc(Cl)cc2O)c(Cl)c1]

According to an aspect of the present invention, a composition for treating a bacterial infection includes the compound of claim 1.

According to an aspect of the present invention, the composition further includes a beta-lactam antibiotic agent.

According to an aspect of the present invention, the antibiotic agent is selected from the group consisting of penicillins, cephems, carbapenems, penems, and monobactams.

According to an aspect of the present invention, the antibiotic agent is selected from the group consisting of penicillins, cephalosporins, cephamycins, monobactams, carbapenems, and a combination thereof.

According to an aspect of the present invention, a method of synthesizing a compound of Formula I of

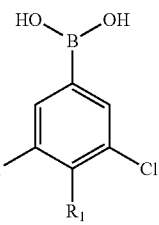

wherein $R_1$ is H,

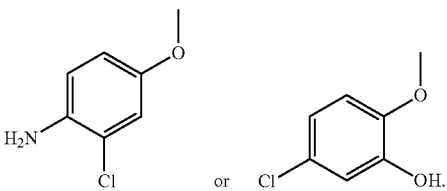

the method includes performing reactions according to one of Reaction Schemes 1 to 3:

Reaction Scheme 1

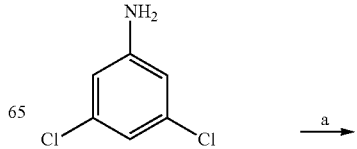

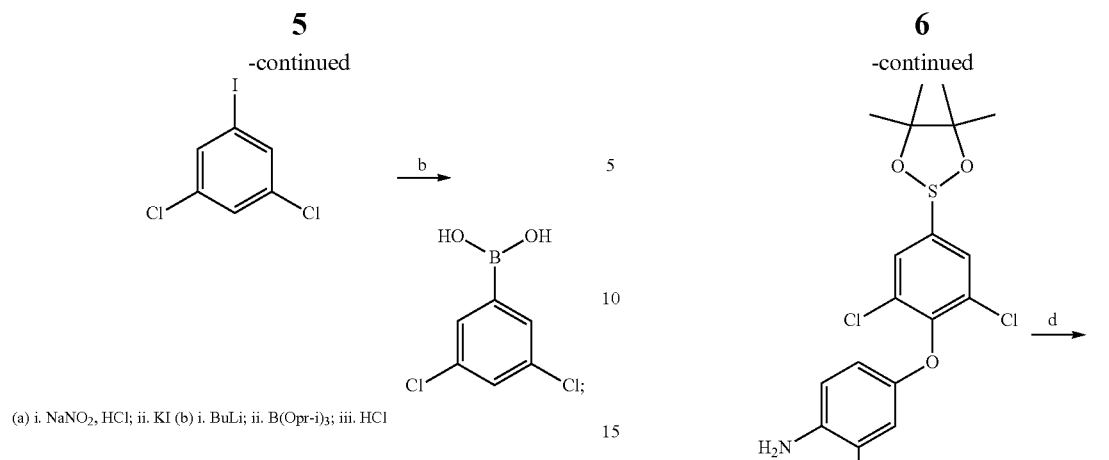
(a) i. NaNO₂, HCl; ii. KI (b) i. BuLi; ii. B(Opr-i)₃; iii. HCl
Reaction Scheme 2
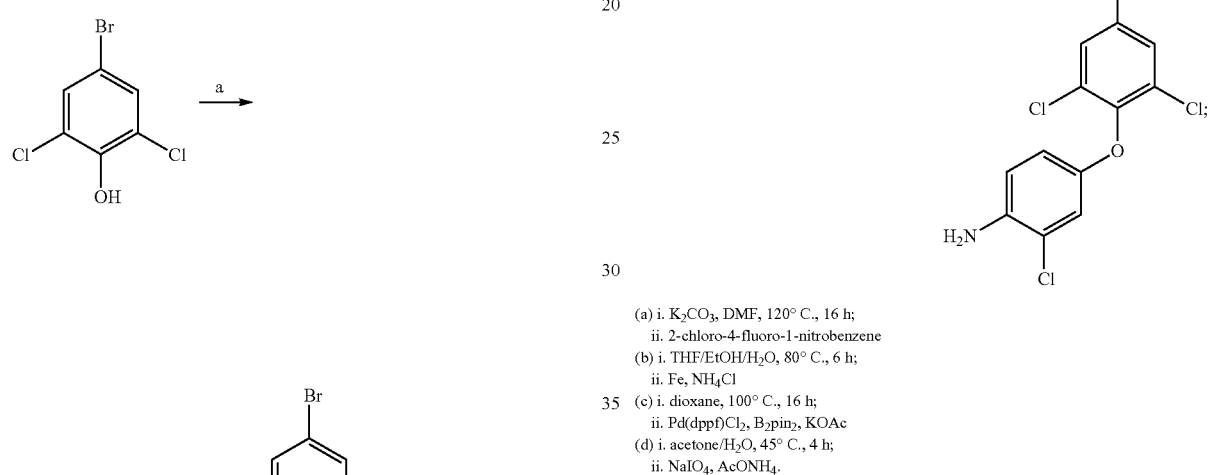
(a) i. K₂CO₃, DMF, 120° C., 16 h;
   ii. 2-chloro-4-fluoro-1-nitrobenzene
(b) i. THF/EtOH/H₂O, 80° C., 6 h;
   ii. Fe, NH₄Cl
(c) i. dioxane, 100° C., 16 h;
   ii. Pd(dppf)Cl₂, B₂pin₂, KOAc
(d) i. acetone/H₂O, 45° C., 4 h;
   ii. NaIO₄, AcONH₄.
and
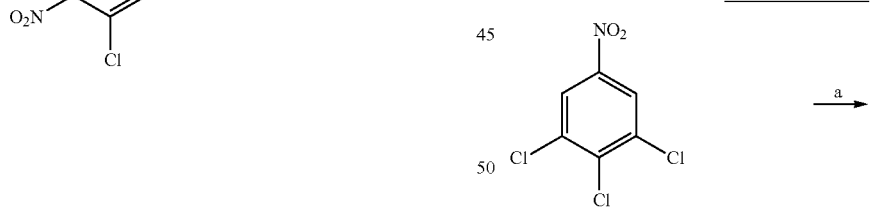
Reaction Scheme 3
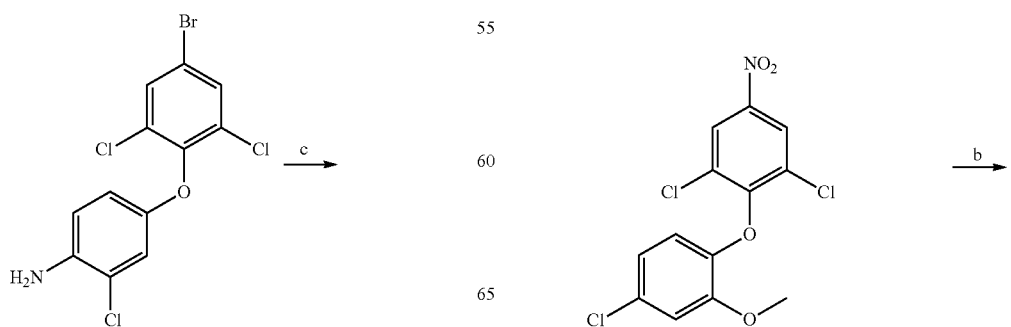

(a) i. K₂CO₃, DMF, 120° C., 16 h;
    ii. 4-cholo-2-methoxyphenol
(b) i. EtOH/H₂O, 75° C., 1 hr;
    ii. Fe, NH₄Cl
(c) i. CuBr, MeCN, 0° C., to RT;
    ii. aq. HBR, NaNO₂
(d) i. Pd(dppf)Cl₂, AcOK, dioxane, 100° C., 16 hr;
    ii. Bis(pinacolato)diboron,
(e) i. Acetone/H₂O, 45° C., 4 hr;
    ii. NaIO₄, AcONH₄
(f) i. BBr₃, DCM, -78° C., to RT, 4 h According to an aspect of the present invention, a method of treating a bacterial infection includes administering to a subject suffering from the bacterial infection a composition comprising an effective amount of a compound having Formula I or a pharmaceutically acceptable derivative thereof:

wherein $R_1$ is H,

According to an aspect of the present invention, the method may further include administering a beta-lactam antibiotic agent to the subject, prior to, simultaneously, or subsequent to administering the composition to the subject.

According to an aspect of the present invention, the composition may further include a pharmaceutically acceptable carrier.

According to an aspect of the present invention, the infection is Gram-negative bacterial infection.

DETAILED DESCRIPTION

Figure 1:
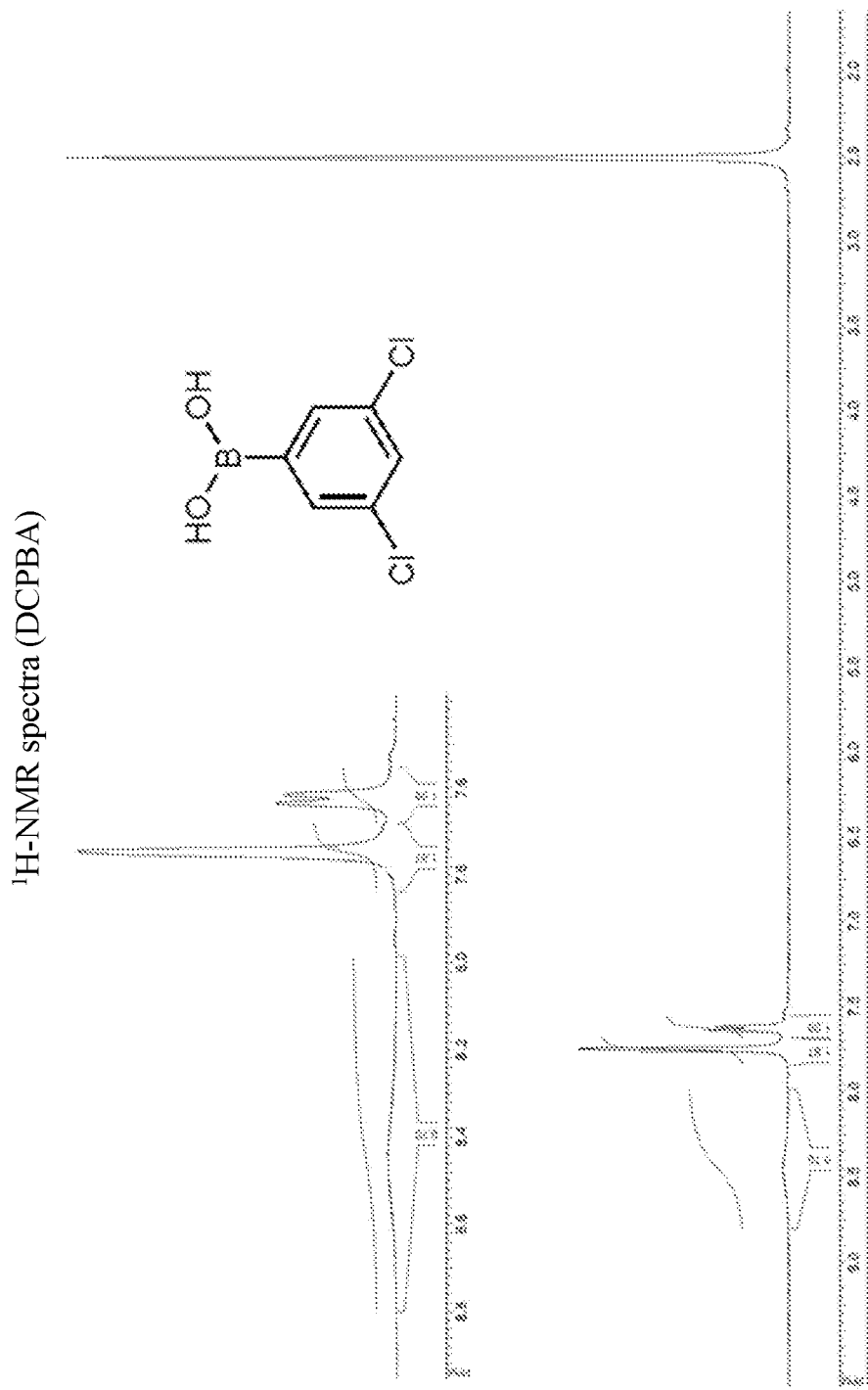
FIG. 1 shows ¹H-NMR spectra of 3,5-Dichlorophenylboronic acid.

Hereinafter embodiments of the present invention will be described in detail with reference to accompanying drawings.

According to one or more embodiments of the present invention, a compound represented by Formula I or its derivative may inhibit MBLs (see Example 3 below). The compound shows broad-spectrum functionality to inhibit all subclasses (B1, B2, and B3) MBLs. However, all reported compounds (FAD-approved) have not been proven to inhibit major clinically-important subclass B1 MBLs (NDM, IMP, VIM, and GIM-types), subclass B2 MBL (CphA), and subclass B3 MBL (GOB-type) (see the Examples below).

Structure-based virtual screening using ICM-VLS software is used to find novel compounds inhibiting MBLs (see Example 1 below). MBLs for use in such screening purified from bacterial sources. The ability ($IC_{50}$ value) of the screened compounds to inhibit MBL activities was determined using the standard enzyme inhibition assay (see Example 5 below; Page, *Biochem. J.*, 295, 295-304 (1993)). Using the cell-based assay, a screen of 6,600 compounds of our chemical library was performed against *K. pneumoniae* harboring bla$_{NDM-1}$ (see Example 2 below). The combination of OCL-4 (screened from our chemical library and composed of parts A and B) and imipenem showed a partial synergy effect against *K. pneumoniae* harboring bla$_{NDM-1}$. To develop novel inhibitors, they were designed based on Formula I (DCPBA with $R_1$=H) and parts (A and B) of OCL-4. ACP-DCPBA was synthesized based on DCPBA and part A of OCL-4 (Scheme 2). CHP-DCPBA was synthesized based on DCPBA and part B of OCL-4 (Scheme 3). In one preferred embodiment of the invention, DCPBA and its derivative compounds (CHP-DCPBA and CHP-DCPBA) can be utilized to effectively inhibit the activity of MBLs.

According to one or more embodiments of the present invention, a composition including the compound of Formula I may be used an inhibitor of metallo-beta-lactamases (MBLs). Unlike all the reported compounds which have not been proven to inhibit all subclasses (B1, B2, and B3) metallo-beta-lactamases (MBLs), the compound of Formula I shows broad-spectrum functionality to inhibit all subclasses (B1, B2, and B3) metallo-beta-lactamases (MBLs).

Therefore, compared with the conventional inhibitors, the compound of Formula I is more effective in inhibiting MBLs so that the compound of Formula I may be more useful for the treatment of bacterial infections.

Since the beta-lactamases of pathogenic bacteria resistant to beta-lactam antibiotics are inactivated by administering the compound of Formula I, the treatment with the antibiotics may be more effectively performed.

Beta-lactam antibiotics (β-lactam antibiotics) are the antibiotic agents that contain a beta-lactam ring in their molecular structure. The beta-lactam antibiotics include, but not limited to, penicillins, cephems, carbapenems, penems, and monobactams. According to an embodiment of the present application, the beta-lactam antibiotics are penicillins, cephalosporins, cephamycins, monobactams, and/or carbapenems.

The composition including the compound of Formula I may be administered either orally or parenterally, and, in case of parenteral administration, the administration can be made by topical application on skin, intravenous injection, subcutaneous injection, muscular injection, intraperitoneal injection, or transdermal administration.

The composition is administered in a pharmaceutically effective amount. As described herein, the expression "pharmaceutically effective amount" means an amount sufficient for treating a bacterial infection that can be applied for a medical treatment. The effective dose level may be determined based on a type or severeness of an infection, activity of a pharmaceutical, sensitivity to a pharmaceutical, administration period, administration route, excretion ratio, time period for therapy, elements including a pharmaceutical used in combination, and other elements that are well known in the medical field. The composition may be administered to a subject, before, simultaneously with, or after administering the beta-lactam antibiotics. The composition can be administered as a separate therapeutic agent, or it can be used in combination with other therapeutic agents. It can be administered in order or simultaneously with a conventional therapeutic agent. It can be also administered as single-dose or multi-dose. It is important to administer an amount which allows obtainment of the maximum effect with minimum dose while considering the all of the aforementioned elements without having any side effect, and the dosage can be easily determined by a person skilled in the pertinent art.

The composition according to an embodiment of the present invention may further include a pharmaceutically acceptable carrier. Included in the carrier are lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methylhydroxy benzoate, propylhydroxy benzoate, talc, magnesium stearate, and mineral oil that are commonly used for having a preparation, but it is not limited thereto. The composition according to an embodiment of the present invention may additionally include a lubricant, a wetting agent, a sweetener, a flavoring agent, an emulsifier, a suspending agent, and a preservative.

The composition of an embodiment of the present invention may be prepared in various formulations including an oral formulation and a parenteral formulation. In case of producing a preparation, production is made by using a diluent or a vehicle such as filler, bulking agent, binding agent, moisturizing agent, disintegrating agent, or surfactant that are commonly used for producing a preparation. As for the solid preparation for oral administration, a tablet, a pill, a powder preparation, a granule, a capsule or the like are included, and such solid preparation is produced by mixing at least one compound with one or more vehicles such as starch, calcium carbonate, sucrose, lactose, or gelatin. Furthermore, other than simple vehicles, a lubricating agent such as magnesium stearate or talc is also used. As for the liquid preparation for oral administration, a suspension, a solution preparation for internal use, an emulsion, a syrup preparation, or the like can be mentioned. Other than water or liquid paraffin as a commonly used simple diluent, various kinds of a vehicle such as moisturizing agent, sweetening agent, aromatic agent, or preservatives may be included. Examples of a preparation for parenteral administration include a sterilized aqueous solution, a non-soluble agent, a suspension agent, an emulsion, a freeze-drying agent, and a suppository agent. As a water insoluble solvent or a suspending agent, propylene glycol, polyethylene glycol, or vegetable oil such as olive oil, and injectable ester such as ethylolate can be used. As a base for a suppository, witepsol, macrogol, tween 61, cacao fat, laurin fat, glycerogelatin, or the like can be used.

Hereinbelow, the present invention is explained in greater detail in view of the Examples. However, the following Examples are given only for specific explanation of the present invention and it wound be evident to a person who has common knowledge in the pertinent art that the scope of the present invention is not limited by them.

Example 1

Virtual Library Screening

To find novel compounds inhibiting the NDM-1 (the most clinically-important MBL), structure-based virtual screening was performed using ICM-VLS software. The crystallographic structure of NDM-1 (PDB ID, 3SPU) (King, et al., Protein Sci., 20, 1484-1491 (2011)) was analyzed using the PocketFinder algorithm available in the Internal Coordinate Mechanics (ICM) software program (Molsoft, LLC).

The protein structure was prepared by three-dimensional (3D) protonation, deletion of water molecules, and energy minimization using the ICM force field and distance-dependent dielectric potential with an RMS (root mean square) gradient of 0.1 Å.

A ligand-binding site was defined as a subset region of 13.0 Å around the active site cleft and was selected as the target site for virtual library screening (VLS) using ICM-VLS software (Molsoft, LLC). ICM-VLS uses global optimization with a biased probability Monte Carlo conformational search to rapidly dock fully flexible, full-atom models of the ligands to a set of grid potential maps calculated from the coordinates of the atoms in the protein receptor. Each ligand-docking conformation is then evaluated with a scoring function. The ICM-scoring function integrates van der Waals energy, electrostatics, hydrogen bonding, conformational entropy loss, and solvation electrostatic energy change (Abagyan, et al., J. Mol. Biol., 235, 983-1002 (1994)). ICM-VLS was used to dock the entire set of 10,658,063 compounds from the MolCart compound and building block database (Molsoft, LLC) using default ICM-docking parameters on three 3.0-GHz Intel Xeon processors. After three separate docking runs, the resulting compounds with a docking score of <−45 were further filtered by selecting those with extensive hydrogen bonds and van der Waals contacts, followed by hierarchical clustering for a diversity of scaffolds, resulting in the identification of 50 compounds highly structurally and chemically compatible with the target NDM-1 ligand-binding site. Seven compounds with the best molecular docking scores were selected and were purchased from the Enamine (http://www.e-namine.net/).

$IC_{50}$ values of seven compounds were determined as described below. The screened seven compounds were dissolved in 100% DMSO at 10 mM. More diluted stocks were prepared as necessary. NDM-1 activity was determined by monitoring the change of absorbance at 482 nm using the characteristic molecular extinction coefficient ($\Delta\varepsilon_{482}$=15,900 $M^{-1}$ $cm^{-1}$) of nitrocefin (NCF) (Oxoid, Hampshire, UK) by a Shimazu UV-1650PC spectrophotometer. Up to 5% DMSO, no influence on the enzyme activities of MBLs was observed. The assays were conducted in 50 mM MES (pH 7.0) containing an enzyme (263 nM), 100 μM $ZnCl_2$, and 100 μg/mL bovine serum albumin. After 5 min of pre-incubation of the purified enzyme and inhibitor at 30° C., the enzymatic reaction was started by adding nitrocefin (100 μM). Residual velocities were determined after 5 minutes. The first 120 s of each reaction was used to measure initial rates. Data were evaluated using Microsoft Excel. Concentration-dependent inhibition of NDM-1 was measured using different concentrations of seven compounds resulting from two-fold dilution series. Reaction progress at every concentration of seven compounds was measured in triplicates. $IC_{50}$ values were calculated using 4-parameter log fits using XL Fit curve fitting software (www.idbs.com) for Excel using the following equation:

$$y = A + \frac{B-A}{1+\left(\frac{x}{IC_{50}}\right)^{slope}}$$

where y is the remaining enzyme activity (in %) and x is the corresponding concentration. The fitted $IC_{50}$ parameter is defined as the concentration giving a response half way between the fitted top (B) and bottom (A) of the curve. Out of the seven compounds, only compound 1 (Formula I: DCPBA) showed $IC_{50}$ value (79.89 μM) (Table 1).

TABLE 1

$IC_{50}$ values on NDM-1 of the screened compounds.

| Compounds | $IC_{50}$ (μM) |
|---|---|
| 1 | 79.89 |
| 2 | NI[a] |
| 3 | NI |
| 4 | NI |
| 5 | NI |
| 6 | NI |
| 7 | NI |

[a]NI, no inhibition.

Example 2

In Vivo Screening

To find enhanced activity of combinations of imipenem (fixed 8 μg/mL) and chemicals, an initial screen of 6,600 compounds of our chemical library was performed at 200 μM in 96-well plates against K. pneumoniae harboring $bla_{NDM-1}$. Briefly, we prepared seeding solutions at a density of 1×10$^7$ cells/mL in Mueller-Hinton II broth (MHB; Difco Laboratories, Detroit, Mich.), and dispensed 10 μL into 96-well plates using multi-channel pipette. We incubated the 96-well plate at 37° C. for 24 h. Then, we determined cell survival using absorbance at Doo and selected compounds that reduced the turbidity of the culture by more than 60% relative to an untreated control. The preliminary screen of 6,600 compounds against K. pneumoniae harboring $bla_{NDM-1}$ yielded four "hits" that reduced cell survival below 60%.

Four compounds (OCL-1, OCL-2, OCL-3, and OCL-4) were tested in checkerboard assays to determine their individual and combination potencies (Table 2). The selected compound combinations in double-dose response experiments were performed to determine the nature of the interaction against *K. pneumoniae* harboring bla$_{NDM-1}$. First, we prepared serial dilutions of each of the selected compounds (20-1280 μg/mL in 10% DMSO) and combined them with serial dilutions of imipenem (10-2560 μg/mL in sterile milli-Q H$_2$O). Next, we prepared a cell-seeding solution at a density of 1×10$^7$ cells/mL in Mueller-Hinton II broth. Lastly, we combined 200 μL of the 96-well plates with final cell, imipenem, and compound concentrations of 5×10$^5$ cells/mL, 0.5-128 μg/mL, and 1-64 μg/mL, respectively. For controls, we seeded a column and row of imipenem or compound alone, as well as untreated and dead cell control wells accordingly. Finally, we incubated the 96-well plates at 37° C. for 24 h and determined cell survival using absorbance at OD$_{600}$. The fractional inhibitory concentration (FIC) index (FIC$_i$) was determined using the following formula: FIC index=FIC$_A$+FIC$_B$=[A]/MIC$_A$+[B]/MIC$_B$, where [A] is the concentration of drug A, MIC$_A$ is its MIC, and FIC$_A$ is the FIC of drug A for the organism, and [B], MIC$_B$, and FIC$_B$ are defined in the same way for drug B. The FIC index thus obtained was interpreted as follows: <0.5, synergy; 0.5 to 0.75, partial synergy; 0.76 to 1.0, additive effect; >1.0 to 4.0, indifference; and >4.0, antagonism (Timurkaynak, et al., *Int. J. Antimicrob. Agents*, 27, 224-228 (2006)). They showed various degrees of increased antibacterial activity when combined with imipenem. In particular, OCL-4 showed the lowest FIC value (0.562) for the combination of imipenem (Table 2). These results indicate that OCL-4 has an inhibitorial effect on NDM-1. To develop inhibitors that can be more effective against *K. pneumoniae* harboring bla$_{NDM-1}$, novel inhibitors were designed based on compound 1 (DCPBA) and parts (A and B) of OCL-4.

TABLE 2

In vitro interaction between imipenem and compounds.

| Compounds | FIC$_i$ | Interaction |
|---|---|---|
| OCL-1 | 0.625 | partial synergy |
| OCL-2 | 0.625 | partial synergy |
| OCL-3 | 0.750 | partial synergy |
| OCL-4 | 0.562 | partial synergy |

Example 3

Synthesis and Characterization of Novel Compounds

Organometallic reactions were performed under argon atmosphere in oven-dried glassware and using anhydrous solvents. Anhydrous tetrahydrofuran (THF) and diethyl ether were obtained by standard methods and freshly distilled under argon from sodium benzophenone ketyl prior to use. All starting chemicals and reagents were commercially available. Chromatographic purification of the compounds was performed on silica gel (particle size 0.05-0.20 mm). $^1$H-NMR and $^{13}$C-NMR spectra were recorded on a Bruker Avance 400 (400 MHz for $^1$H and 125 MHz for $^{13}$C) or Bruker Avance 500 (500 MHz for $^1$H and 125 MHz for $^{13}$C) spectrometer in methanol (CD$_3$OD) solutions. Chemical shifts (δ) are reported in ppm downfield from tetramethylsilane (TMS) as internal standard (s singlet, d doublet, t triplet, m multiplet, br s broad signal). Coupling constants (J) are given in Hz. The purity of the obtained compounds was checked by LC/MS on an Agilent 1260 instrument. The purity of all tested compounds was above 95%.

Example 3-1: Synthesis of 3,5-Dichlorophenylboronic Acid (DCPBA; Compound 1)

An exemplary synthesis of the compound of Formula I is as follows:

Scheme 1: Synthesis of DCPBA.

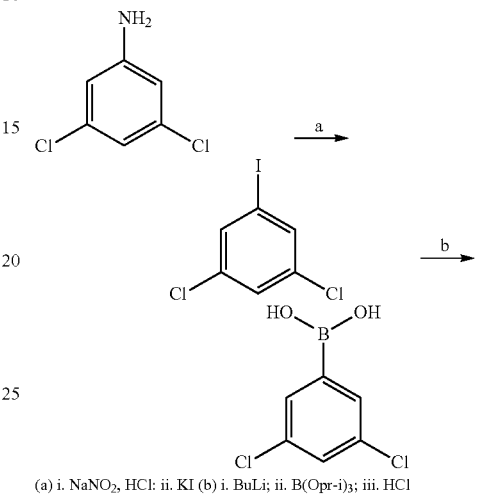

(a) i. NaNO$_2$, HCl: ii. KI (b) i. BuLi; ii. B(Opr-i)$_3$; iii. HCl

Step 1:

The 3,5-dichloroaniline (0.042 mol) was added to concentrated hydrochloric acid (300 mL) and the mixture was cooled to −5° C. A solution of sodium nitrite (0.24 mol) in water (90 mL) was added dropwise with vigorous stirring, maintaining the reaction temperature in a range of −5° C. to 0° C. After 30 min, the mixture was filtered, and the filtrate was added to a cooled (0° C.) and stirred solution of potassium iodide (0.6 mol) in water (60 mL). The mixture was warmed to room temperature (RT) and stirred overnight. The reaction was diluted with ethyl acetate (300 mL), and the organic phase was separated, and the aqueous phase was extracted with ethyl acetate (1×200 mL). The combined organic extracts were washed with a saturated solution of NaHSO$_3$, dried over Na$_2$SO$_4$, and concentrated under reduced pressure. The residue was purified by column chromatography on silica gel (hexane/ethyl acetate 50:1), affording the 1,3-dichloro-5-iodobenzene.

Figure 2:
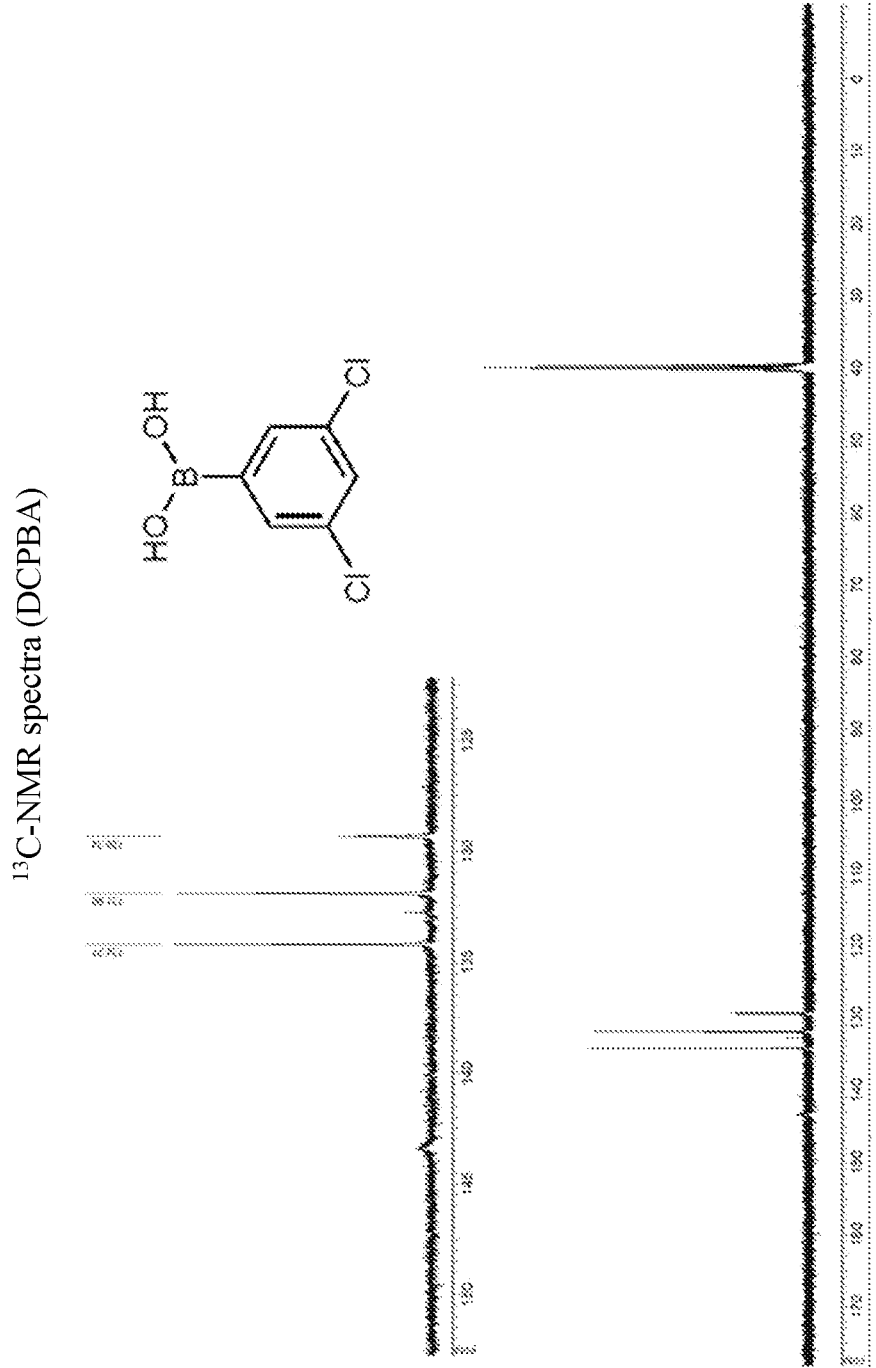
FIG. 2 shows $^{13}$C-NMR spectra of 3,5-Dichlorophenylboronic acid.

Step 2:

A stirred solution of 0.026 mol of the iodide (1,3-dichloro-5-iodobenzene) in 150 mL of THF was cooled to −80° C. and 0.029 mol of n-butyllithium (BuLi) in hexane (2.5 M) was added dropwise, while maintaining the reaction mixture temperature below −70° C. Upon completion of the addition, the reaction mixture was stirred at −80° C. for 15 min and then 0.076 mol of triisopropyl borate was added at once. The reaction mixture was allowed to warm slowly to ambient temperature and was stirred for an additional 1 h. After this time, the reaction mixture was concentrated under reduced pressure to a volume of about 50 mL and was poured into 500 mL of ice-water. The mixture was acidified with 26 mL of aqueous 2 N hydrochloric acid and the precipitate formed was filtered and dried yielding the target compound as a white powder. Mp 323° C. LC/MS: MH$^+$192. $^1$H-NMR (500 MHz, DMSO): δ7.62 (d, 1H, 4-H), 7.76 (s, 2H, 2,6-H), 8.44 (br s, 2H, OH) (FIG. 1). $^{13}$C-NMR (125 MHz, DMSO): δ129.3 (4-C), 131.9 (2,6-C), 132.8 (1-C), 134.2 (3,5-C) (FIG. 2).

Example 3-2: Synthesis of (4-(4-amino-3-chlorophenoxy)-3,5-dichlorophenyl)boronic Acid (ACP-DCPBA)

Figure 3:
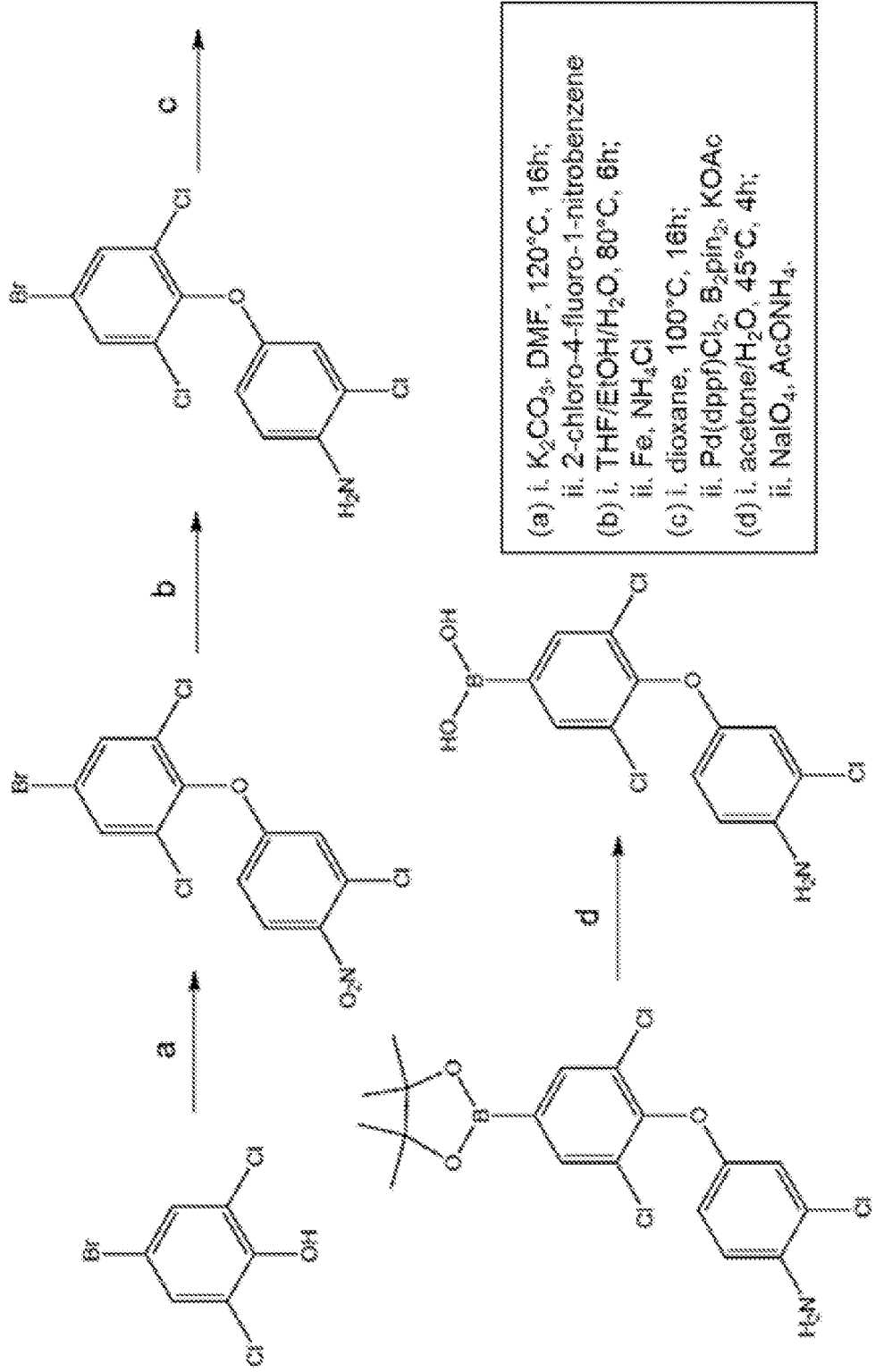
FIG. 3 is a schemes and reagents of flow sheet showing an exemplary synthesis of the ACP-DCPBA compound.
Figure 4:
FIG. 4 shows $^1$H-NMR spectra of (4-(4-amino-3-chlorophenoxy)-3,5-dichlorophenyl) boronic acid.
Figure 5:
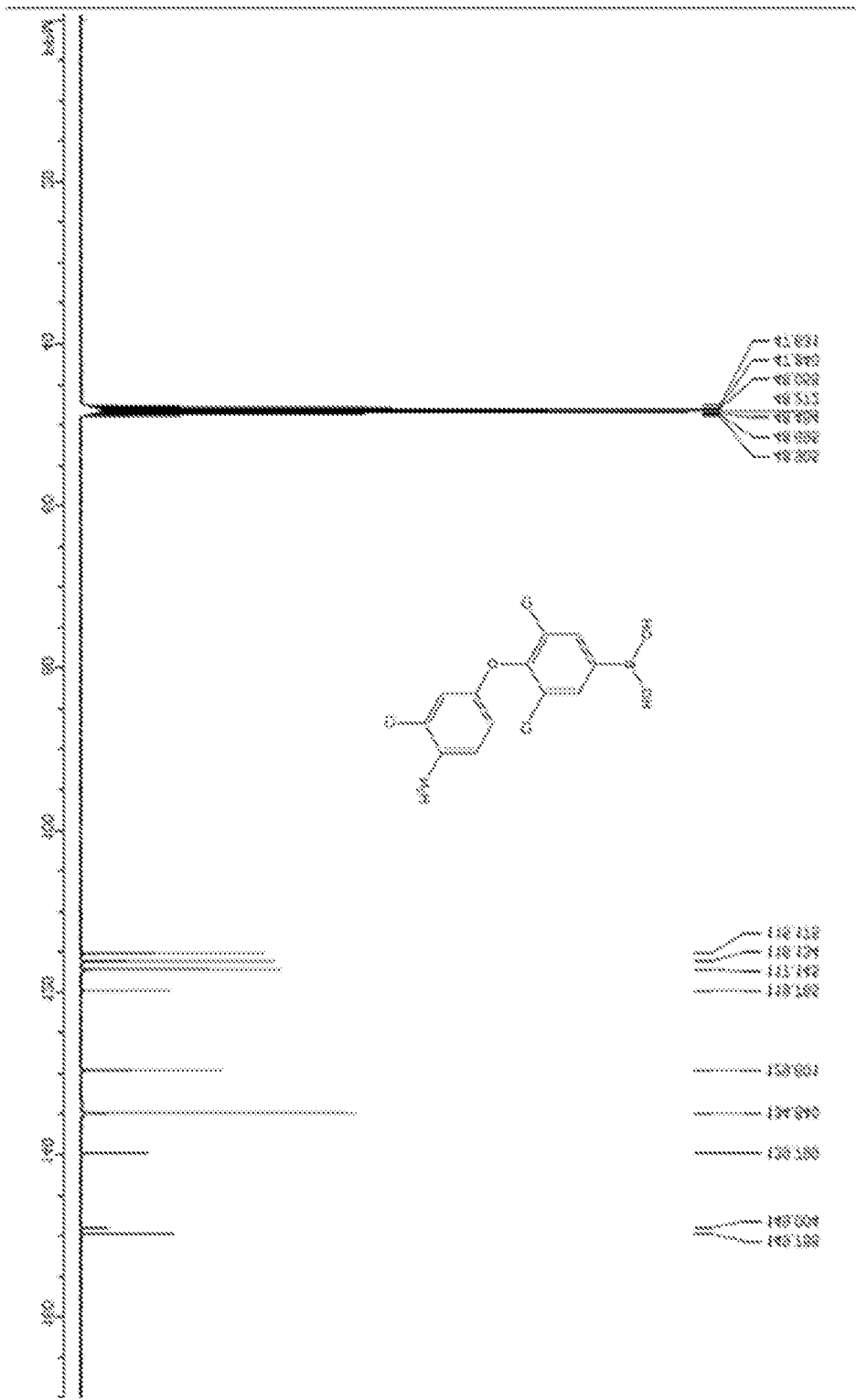
FIG. 5 shows $^{13}$C-NMR spectra of 4-(4-amino-3-chlorophenoxy)-3,5-dichlorophenyl) boronic acid.

An exemplary synthesis of the ACP-DCPBA compound of the present invention was synthesized by following the schemes and reagents of flow sheet as shown in FIG. 3.
Scheme 2: Synthesis of ACP-DCPBA
Step 1:
To a solution of 4-bromo-2,6-dichlorophenol (30.2 g, 124.8 mmol, 1.05 eq) in DMF (200 mL) was added 2-chloro-4-fluoro-1-nitrobenzene (20.9 g, 121.5 mmol, 1.0 eq) and K$_2$CO$_3$ (32.8 g, 237.7 mmol, 2.0 eq). The resulting mixture was stirred for 16 hrs at 120° C. Then the mixture was filtered, and the filtrate was diluted with water (1000 mL), extracted with EA (300 mL×3). The combined organic layer was washed with brine (400 mL×3), dried over anhydrous sodium sulfate and concentrated in vacuum. The residue was purified by silica gel column eluting with PE/EA=100/1 to afford 5-bromo-1,3-dichloro-2-(3-chloro-4-nitrophenoxy) benzene as a white solid (6.6 g, pure, yield: 14%) and yellow solid (18.5 g, purity: about 70%, yield: 39%).
Step 2:
To a solution of 5-bromo-1,3-dichloro-2-(3-chloro-4-nitrophenoxy)benzene (18.5 g, 46.6 mmol, 1.0 eq) in a mixture solvents of THF (230 mL), EtOH (115 mL) and H$_2$O (58 mL) was added NH$_4$Cl (25.2 g, 466.0 mol, 10 eq) and Fe (13.0 g, 233.0 mmol, 5 eq). The resulting mixture was stirred at 80° C. for 6 hrs. The reaction was monitored by LC-MS. Then the mixture was filtered and the filtrate was concentrated. The residue was diluted with H$_2$O (150 mL) and extracted with EA (200 mL×3). The combined organic layer was washed with brine (100 mL) and dried over anhydrous sodium sulfate. The solution was concentrated in vacuum and the residue was purified by silica flash column (010% EA in PE) to afford 4-(4-bromo-2,6-dichlorophenoxy)-2-chloroaniline as a white solid (8.3 g, yield: 48%).
Step 3:
To a mixture of 4-(4-bromo-2,6-dichlorophenoxy)-2-chloroaniline (8.3 g, 22.6 mmol, 1.0 eq), B$_2$pin$_2$ (6.9 g, 27.1 mmol, 1.2 eq) and KOAc (4.4 g, 45.2 mmol, 2.0 eq) in dioxane (170 mL) under nitrogen was added Pd(dppf)Cl$_2$ (1.7 g, 2.3 mmol, 0.1 eq). The resulting mixture was stirred at 100° C. for 16 hrs. The reaction was monitored by LC-MS. Then the mixture was concentrated in vacuum. The residue was purified by silica gel column eluting with PE/EA=30/1 to afford 2-chloro-4-(2,6-dichloro-4-(4,4,5,5-tetramethyl-1,3,2-dioxaborolan-2-yl)phenoxy)aniline as a white solid (6.8 g, yield: 73%).
Step 4:
To a solution of 2-chloro-4-(2,6-dichloro-4-(4,4,5,5-tetramethyl-1,3,2-dioxaborolan-2-yl)phenoxy)aniline (6.8 g, 16.5 mmol) in acetone (200 mL) was added H$_2$O (50 mL), NaIO$_4$ (28.2 g, 131.7 mmol) and AcONH$_4$ (10.1 g, 131.7 mmol). After being stirred at 45° C. for 4 hrs, the mixture was concentrated, diluted with MeOH (50 mL) and filtered to remove insoluble solid. The filtrate was purified by reverse phase column (10% 100% MeCN in H$_2$O) to give (4-(4-amino-3-chlorophenoxy)-3,5-dichlorophenyl)boronic acid (3.5 g, yield: 64%) as a brownish red solid. $^1$H-NMR (400 MHz, CD$_3$OD): δ 6.58 (dd, J=8.8, 2.8 Hz, 1H), 6.67 (d, J=2.8 Hz, 1H), 6.80 (d, J=8.8 Hz, 1H), 7.76 (brs, 2H) (FIG. 4). $^{13}$C-NMR (400 MHz, CD$_3$OD): δ=115.18, 116.13, 117.15, 119.77, 129.60, 134.84, 139.80, 149.00, 149.79. MS: m/z 331.9 [M+H]$^+$ (FIG. 5).

Example 3-3: Synthesis of (3,5-dichloro-4-(2-hydroxyethoxy)phenyl)boronic Acid (CHP-DCPBA)

Figure 6:
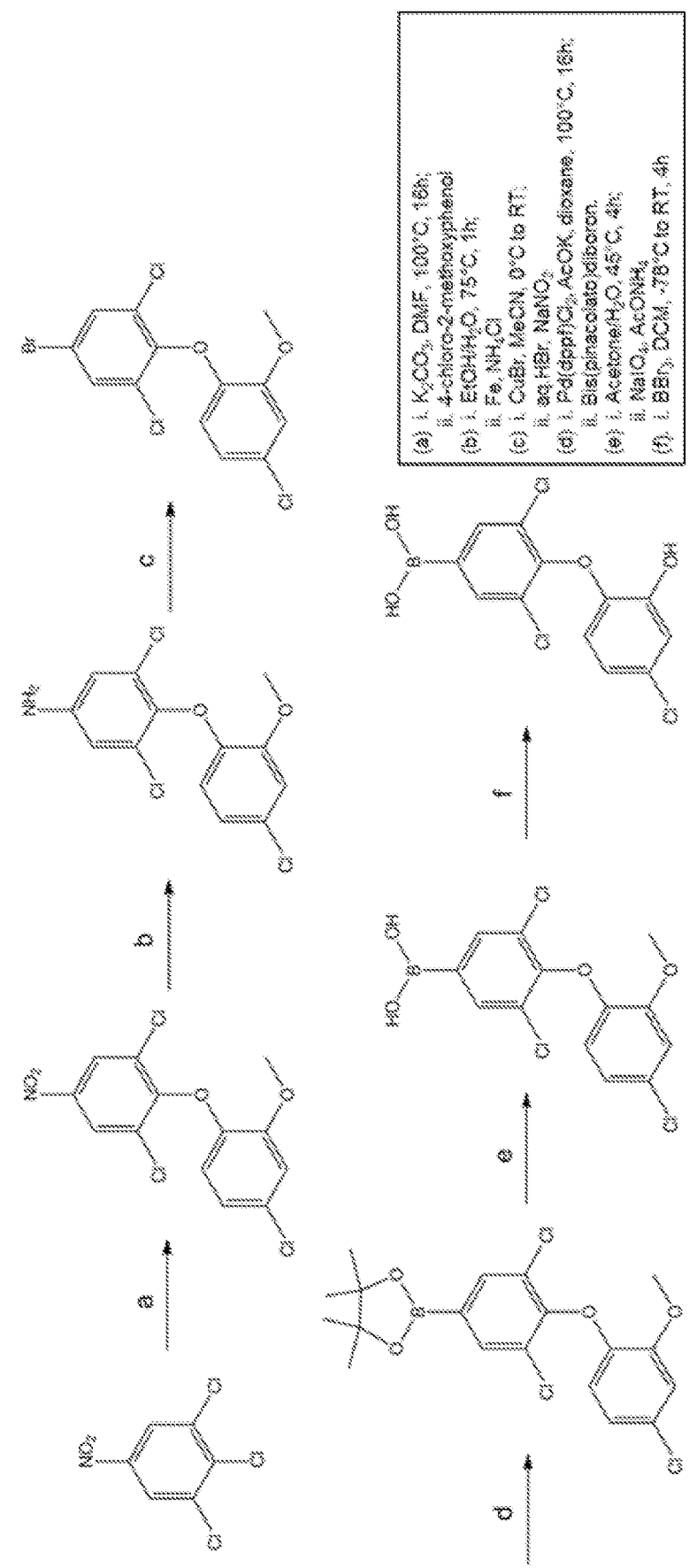
FIG. 6 is a schemes and reagents of flow sheet showing an exemplary synthesis of the CHP-DCPBA compound.

An exemplary synthesis of the CHP-DCPBA compound of the present invention was synthesized by following the schemes and reagents of flow sheet as shown in FIG. 6:
Scheme 3: Synthesis of CHP-DCPBA.
Step 1:
To a solution of 1,2,3-trichloro-5-nitrobenzene (7.0 g, 31.0 mmol) in DMF (100 mL) was added 4-chloro-2-methoxyphenol (4.9 g, 31.0 mmol) and K$_2$CO$_3$ (8.6 g, 62.0 mmol). After being stirred at 100° C. for 16 hrs, the mixture was diluted with water (400 mL) and extracted with EA (200 mL×3). The combined EA was washed with brine (300 mL×3), dried over Na$_2$SO$_4$ and concentrated under vacuum. The residue was triturated with PE/EA=20/1 (120 mL) to give 1,3-dichloro-2-(4-chloro-2-methoxyphenoxy)-5-nitrobenzene (9.2 g, yield: 86%) as a yellow solid. $^1$H-NMR (400 MHz, CDCl$_3$): δ=3.91 (s, 3H), 6.45 (d, J=8.8 Hz, 1H), 6.81 (dd, J=8.4, 2.4 Hz, 1H), 6.99 (d, J=2.4 Hz, 1H), 8.28 (s, 2H).
Step 2:
To a solution of 1,3-dichloro-2-(4-chloro-2-methoxyphenoxy)-5-nitrobenzene (9.2 g, 26.6 mmol) in THF/EtOH/H$_2$O (50 mL/100 mL/20 mL) was added Fe (7.5 g, 133.3 mmol) and NH$_4$Cl (14.4 g, 266.6 mmol). After being stirred at 75° C. for 1 hr, the reaction mixture was concentrated to about 50 mL, diluted with EA/H$_2$O (100 mL/100 mL) and filtered. The water phase was separated and extracted with EA (100 mL). The combined organic layer was washed by brine (50 mL), dried over Na$_2$SO$_4$ and concentrated to give 3,5-dichloro-4-(4-chloro-2-methoxyphenoxy)aniline (8.2 g, yield: 97%) as a yellow solid.
Step 3:
A solution of 3,5-dichloro-4-(4-chloro-2-methoxyphenoxy)aniline (8.0 g, 25.2 mmol) in MeCN (180 mL) was treated with 40% aq·HBr (15.1 mL, 75.7 mmol). To the resulting mixture was added a solution of NaNO$_2$ (2.1 g, 30.3 mmol) in H$_2$O (30 mL) dropwise at −5° C. After addition, the mixture was stirred at −5° C. for 25 mins. CuBr (7.2 g, 50.5 mmol) was added portion wise. The mixture was allowed to warm to room temperature and stirred for another 1 hr. Then the mixture was concentrated to about 30 mL and diluted with H$_2$O (100 mL), extracted with EA (100 mL×2). The combined EA was washed with brine (100 mL), dried over Na$_2$SO$_4$ and concentrated. The residue was purified by silica gel column (PE/EA=80/1) to give 5-bromo-1,3-dichloro-2-(4-chloro-2-methoxyphenoxy)benzene (7.5 g, yield: 78%) as a white solid. $^1$H-NMR (400 MHz, CDCl$_3$): δ 3.95 (s, 3H), 6.34 (d, J=8.8 Hz, 1H), 6.77 (dd, J=8.8, 2.4 Hz, 1H), 6.98 (d, J=2.0 Hz, 1H), 7.54 (s, 2H).
Step 4:
A mixture of 5-bromo-1,3-dichloro-2-(4-chloro-2-methoxyphenoxy)benzene (7.5 g, 19.7 mmol), bis(pinacolato)diboron (7.5 g, 29.6 mmol), Pd(dppf)Cl$_2$ (720 mg, 1.0 mmol) and AcOK (3.9 g, 39.5 mmol) in dioxane (115 mL) was stirred at 100° C. for 16 hrs under N$_2$ atmosphere. Then the mixture was concentrated and purified by silica gel column (PE/EA=80/1) to give 2-(3,5-dichloro-4-(4-chloro-2-methoxyphenoxy)phenyl)-4,4,5,5-tetramethyl-1,3,2-dioxaborolane (7.1 g, yield: 84%) as a white solid.

Figure 7:
FIG. 7 shows $^1$H-NMR spectra of (3,5-dichloro-4-(2-hydroxyethoxy)phenyl)boronic acid.
Figure 8:
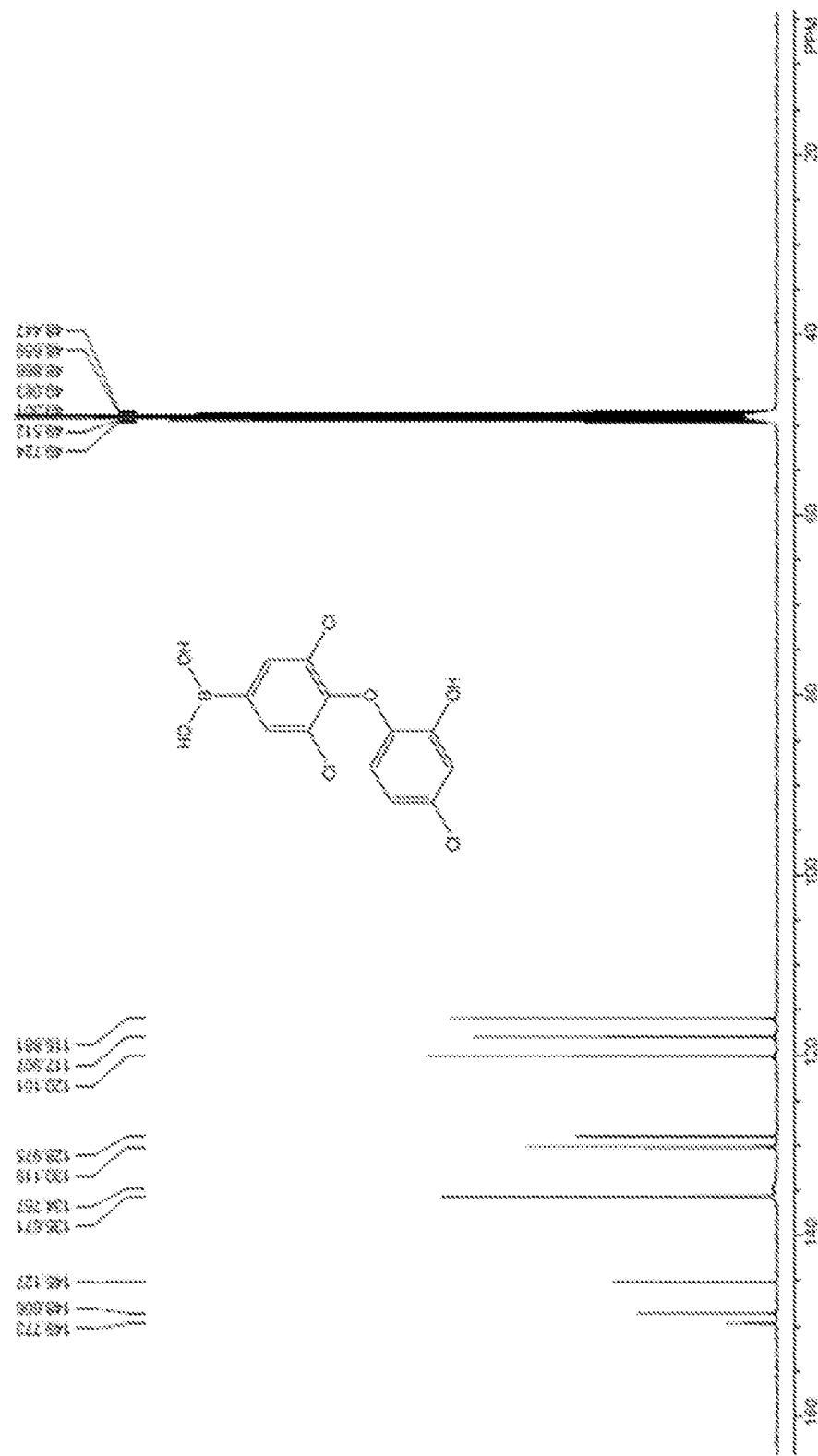
FIG. 8 shows $^{13}$C-NMR spectra of (3,5-dichloro-4-(2-hydroxyethoxy)phenyl)boronic acid.

Step 5:

To a solution of 2-(3,5-dichloro-4-(4-chloro-2-methoxyphenoxy)phenyl)-4,4,5,5-tetramethyl-1,3,2-dioxaborolane (4.0 g, 9.3 mmol) in acetone (160 mL) was added $H_2O$ (40 mL), $NaIO_4$ (16.0 g, 74.8 mmol) and $AcONH_4$ (5.8 g, 74.8 mmol). After being stirred at 45° C. for 4 hrs, the mixture was concentrated, diluted with MeOH (50 mL) and filtered to remove insoluble solid. The filtrate was concentrated to about 30 mL and purified by reverse phase column (30%~100% MeCN in $H_2O$) to give (3,5-dichloro-4-(4-chloro-2-methoxyphenoxy)phenyl)boronic acid (2.6 g, yield: 80%) as a white solid. MS: m/z 345.3 $(M-H)^-$ Step 6:

A solution of $BBr_3$ in DCM (17%, 30 mL, 30.0 mmol) was added dropwise to a stirred solution of (3,5-dichloro-4-(4-chloro-2-methoxyphenoxy)phenyl)boronic acid (2.5 g, 7.5 mmol) in DCM (60 mL) at −78° C. under an atmosphere of $N_2$. The reaction was allowed to warm to room temperature within 1 hr and stirred for another 3 hrs. The reaction was quenched with MeOH (20 mL) at −78° C. and stirred at room temperature for 10 mins. The resulting solution was concentrated under vacuum. The residue was purified by reverse phase column (5%~95% MeCN in $H_2O$) to give (3,5-dichloro-4-(4-chloro-2-hydroxyphenoxy)phenyl)boronic acid (2.0 g, yield: 83%) as a white solid. $^1$H-NMR (400 MHz, $CD_3OD$): δ 6.28 (d, J=8.8 Hz, 1H), 6.65 (dd, J=8.8, 2.4 Hz, 1H), 6.93 (d, J=2.4 Hz, 1H), 7.79 (brs, 2H) (FIG. 7). $^{13}$C-NMR (400 MHz, $CD_3OD$): δ 115.88, 117.91, 120.10, 128.98, 130.12, 134.77, 135.67, 145.13, 148.61, 149.77. MS: m/z 332.9 $(M+H)^+$ (FIG. 8).

Example 4

Protein Production and Purification

The $bla_{NDM-1}$ gene (GenBank ID: FN396876) from *K. pneumoniae* clinical isolate, $bla_{IMP-1}$ gene (GenBank ID: S71932) from *Acinetobacter baumannii* clinical isolate, and $bla_{VIM-2}$ gene (GenBank ID: AF191564) from *Citrobacter freundii* clinical isolate were cloned after PCR amplification with primer pairs (Table 3) and then sequenced. Those three clinical isolates were collected from a university hospital in the Republic of Korea. Three DNA templates encoding $bla_{GIM-1}$ gene (GenBank ID: AJ620678), $blac_{phA}$ gene (GenBank ID: X57102), and $bla_{GOB-1}$ gene (GenBank ID: AF090141), which are codon optimized for *E. coli*, were synthesized and purchased from IDT (Integrated DNA Technologies, Coralville, Iowa, USA). The DNA templates were amplified by PCR using suitable primer pairs (Table 3). The amplified DNA and pET-30a(+) vector (Novagen, Madison, Wis., USA) were double-digested with NdeI and XhoI, with digested DNA then ligated into the digested vector. After verifying the DNA sequences, the plasmids, pET-30a(+)/$His_6$-$bla_{NDM-1}$, pET-30a(+)/$His_6$-$bla_{IMP-1}$, pET-30a(+)/$His_6$-$bla_{VIM-2}$, pET-30a(+)/$His_6$-$bla_{GIM-1}$, pET-30a(+)/$His_6$-$blac_{phA}$, and pET-30a(+)/$His_6$-$bla_{GOB-1}$ were individually transformed into *E. coli* BL21 (DE3) cells. Each of the histidine-tagged proteins, NDM-1, IMP-1, VIM-2, GIM-1, CphA, and GOB-1 were prepared as previously described (Park, et al., *J. Glob. Antimicrob. Resist.*, 14, 302-305 (2018)).

TABLE 3

Nucleotide sequences of the oligonucleotides used for PCR amplification to express six genes encoding MBLs.

| Name | Primer name[a] | Sequence (5'→3') |
| --- | --- | --- |
| NDM-1 | NdeI-HIis-EK-NDM-1-F | 5'-ATACATATGCACCATCATCATCATCAT*GAC GACGACGAC*AAGGAAATCCGCCCGACGATTGGC CAGCAA-3' (SEQ ID NO: 1) |
|  | XhoI-NDM-1-R | 5'-GAGCTCGAGTCAGCGCAGCTTGTCGGCCAT GCGGGCCGTATGA-3' (SEQ ID NO: 2) |
| IMP-1 | NdeI-His-EK-IMP-1-F | 5'-ATACATATGCACCATCATCATCATCAT*GAC GACGACGAC*AAGTCTTTGCCAGATTTAAAAATT GAAAAGCTTG-3' (SEQ ID NO: 3) |
|  | XhoI-IMP-1-R | 5'-GAGCTCGAGTTAGTTGCTTGGTTTTGATGG TTTTTTAC-3' (SEQ ID NO: 4) |
| VIM-2 | NdeI-His-EK-VIM-2-F | 5'-ATACATATGCACCATCATCATCATCAT*GAC GACGACGAC*AAGGAGTATCCGACAGTCAGCGAA ATTC-3' (SEQ ID NO: 5) |
|  | XhoI-VIM-2-R | 5'-GAGCTCGAGCTACTCAACGACTGAGCGATT TGTG-3' (SEQ ID NO: 6) |
| GIM-1 | NdeI-HIis-EK-GIM-1-F | 5'-ATACATATGCACCATCATCATCATCAT*GAC GACGACGAC*AAGCAGGGTCATAAACCGCTAGAA GTTA-3' (SEQ ID NO: 7) |
|  | XhoI-GIM-1-R | 5'-GAGCTCGAGTTAATCAGCCGACGCTTCAGC G-3' (SEQ ID NO: 8) |
| CphA | NdeI-His-EK-CphA-F | 5'-ATACATATGCACCATCATCATCATCAT*GAC GACGACGAC*AAGGCGGGGATGTCGCTGACGCA-3' (SEQ ID NO: 9) |
|  | XhoI-CphA-R | 5'-GAGCTCGAGTTATGACTGGGGTGCGGCCTT GATCAG-3' (SEQ ID NO: 10) |
| GOB-1 | NdeI-His-EK-GOB-1-F | 5'-ATACATATGCACCATCATCATCATCAT*GAC GACGACGAC*AAGCAGGTGGTTAAGGAACCGGA G-3' (SEQ ID NO: 11) |
|  | XhoI-GOB-1-R | 5'-GAGCTCGAGTTATTTGTCTTGCGAGTCCTT TTTTATTTTGTC-3' (SEQ ID NO: 12) |

[a]F, sense (forward) primer; R, antisense (reverse) primer.
Restriction sites appear in bold.
The underlined and bolded bases indicate the hexahistidine tag, and italic bases indicate the enterokinase recognition site.

Example 5

The Determination of $IC_{50}$ Values of the Novel Compounds (DCPBA, ACP-DCPBA, and CHP-DCPBA) for MBLs To investigate the inhibitory effects of novel compounds (DCPBA, ACP-DCPBA, and CHP-DCPBA) against four clinically-important subclass B1 MBLs (NDM-1, IMP-1, VIM-2, and GIM-1), subclass B2 MBL (CphA), and subclass B3 MBL (GOB-1), the $IC_{50}$ values for them were determined (Table 4). Compounds (DCPBA, ACP-DCPBA, and CHP-DCPBA) were dissolved in 100% DMSO at 10 mM. Activities of MBLs were determined by monitoring the change of absorbance at 482 nm. Up to 5% DMSO, no influence on the enzyme activities of MBLs was observed. Each enzyme (NDM-1, 263 nM; IMP-1, 891 nM; VIM-2, 81 nM; GIM-1, 662 nM; CphA, 157 nM; GOB-1, 2.69 μM) was mixed with 100 μM nitrocefin after a 5 minute pre-incubation with compounds (DCPBA, ACP-DCPBA, and CHP-DCPBA). The first 120 s of each reaction was used to measure initial rates. Data were evaluated using Microsoft Excel. Reaction progress at every concentration of DCPBA (ACP-DCPBA or CHP-DCPBA) was measured in triplicates. The results of the inhibition of MBLs by DCPBA, ACP-DCPBA, and CHP-DCPBA are shown in Table 4. DCPBA showed $IC_{50}$ values in the 27.33±0.01 μM~798.90±0.02 μM ranges for all subclasses MBLs. ACP-DCPBA showed $IC_{50}$ values in the 22.78±0.01 μM~790.24±0.02 μM ranges for all subclasses MBLs. CHP- DCPBA showed IC$_{50}$ values in the 15.15±0.01 µM~468.50±0.01 µM ranges for all subclasses MBLs. Therefore, all novel compounds (DCPBA, ACP-DCPBA, and CHP-DCPBA) showed inhibitory effects on all subclasses MBLs. In particular, IC$_{50}$ values of CphA for ACP-DCPBA and CHP-DCPBA were six-fold lower than that of CphA for DCPBA. Table 4 demonstrates that CHP-DCPBA is the best inhibitor of all subclasses (B1, B2, and B3) metallo-beta-lactamases.

TABLE 4

IC$_{50}$ values for novel inhibitors (DCPBA, ACP-DCPBA, and CHP-DCPBA) against all subclasses (B1, B2, and B3) MBLs with nitrocefin as a substrate.

| | IC$_{50}$ (µM) | | | | | |
|---|---|---|---|---|---|---|
| | Subclass B1 MBLs[a] | | | | Subclass B2 MBL | Subclass B3 MBL |
| Inhibitors | NDM-1 | IMP-1 | VIM-2 | GIM-1 | CphA | GOB-1 |
| DCPBA | 79.89 ± 0.03 | 738.88 ± 0.01 | 27.33 ± 0.01 | 144.64 ± 0.01 | 530.87 ± 0.02 | 798.90 ± 0.02 |
| ACP-DCPBA | 78.78 ± 0.01 | 738.41 ± 0.01 | 22.78 ± 0.01 | 144.64 ± 0.01 | 90.19 ± 0.01 | 790.24 ± 0.02 |
| CHP-DCPBA | 37.77 ± 0.01 | 468.30 ± 0.01 | 15.15 ± 0.01 | 81.35 ± 0.03 | 80.81 ± 0.01 | 468.50 ± 0.01 |

[a]MBLs, metallo-beta-lactamases

It was proven that the compound of Formula I shows broad-spectrum functionality to inhibit all clinically important MBLs subgroups.

The compounds are therefore useful in potentiating the effects of beta-lactam antibiotic agents (beta-lactams) and can be used in combination with beta-lactam antibiotic agents in the prevention and treatment of bacterial infections.

What is claimed is:

1. A method of treating a bacterial infection, the method comprising: administering to a subject suffering from the bacterial infection a composition comprising an effective amount of a compound having Formula I or a pharmaceutically acceptable derivative thereof:

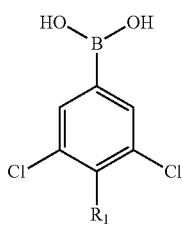

Formula I wherein R1 is

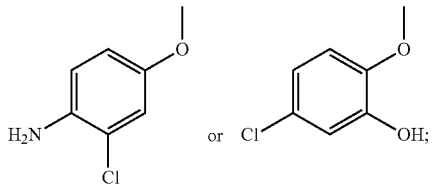

and further comprising administering to the subject a beta-lactam antibiotic agent selected from the group consisting of penicillins, cephalosporins, cephamycins, monobactams, carbapenems, and a combination thereof.

2. The method of claim 1, wherein the compound is

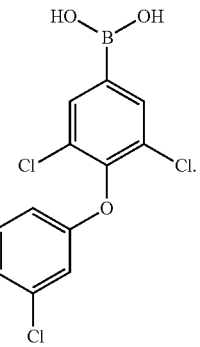

3. The method of claim 1, wherein the compound is

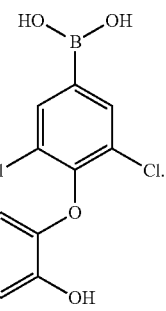

4. The method of claim 1, wherein the composition further comprises a pharmaceutically acceptable carrier.

5. The method of claim 1, wherein the infection is Gram-negative bacterial infection.

* * * * *

SEQUENCE LISTING

<160> NUMBER OF SEQ ID NOS: 12

<210> SEQ ID NO 1
<211> LENGTH: 69
<212> TYPE: DNA
<213> ORGANISM: Artificial Sequence
<220> FEATURE:
<223> OTHER INFORMATION: Primer

<400> SEQUENCE: 1
atacatatgc accatcatca tcatcatgac gacgacgaca aggaaatccg cccgacgatt      60
ggccagcaa                                                             69

<210> SEQ ID NO 2
<211> LENGTH: 43
<212> TYPE: DNA
<213> ORGANISM: Artificial Sequence
<220> FEATURE:
<223> OTHER INFORMATION: primer

<400> SEQUENCE: 2
gagctcgagt cagcgcagct tgtcggccat gcgggccgta tga                       43

<210> SEQ ID NO 3
<211> LENGTH: 73
<212> TYPE: DNA

```
<213> ORGANISM: Artificial Sequence
<220> FEATURE:
<223> OTHER INFORMATION: primer

<400> SEQUENCE: 3
atacatatgc accatcatca tcatcatgac gacgacgaca agtctttgcc agatttaaaa      60
attgaaaagc ttg                                                        73

<210> SEQ ID NO 4
<211> LENGTH: 38
<212> TYPE: DNA
<213> ORGANISM: Artificial Sequence
<220> FEATURE:
<223> OTHER INFORMATION: primer

<400> SEQUENCE: 4
gagctcgagt tagttgcttg gttttgatgg ttttttac                             38

<210> SEQ ID NO 5
<211> LENGTH: 67
<212> TYPE: DNA
<213> ORGANISM: Artificial Sequence
<220> FEATURE:
<223> OTHER INFORMATION: primer

<400> SEQUENCE: 5
atacatatgc accatcatca tcatcatgac gacgacgaca aggagtatcc gacagtcagc      60
gaaattc                                                               67

<210> SEQ ID NO 6
<211> LENGTH: 34
<212> TYPE: DNA
<213> ORGANISM: Artificial Sequence
<220> FEATURE:
<223> OTHER INFORMATION: primer

<400> SEQUENCE: 6
gagctcgagc tactcaacga ctgagcgatt tgtg                                 34

<210> SEQ ID NO 7
<211> LENGTH: 67
<212> TYPE: DNA
<213> ORGANISM: Artificial Sequence
<220> FEATURE:
<223> OTHER INFORMATION: primer
```

-continued

<400> SEQUENCE: 7
atacatatgc accatcatca tcatcatgac gacgacgaca agcagggtca taaaccgcta    60
gaagtta    67

<210> SEQ ID NO 8
<211> LENGTH: 31
<212> TYPE: DNA
<213> ORGANISM: Artificial Sequence
<220> FEATURE:
<223> OTHER INFORMATION: primer

<400> SEQUENCE: 8
gagctcgagt taatcagccg acgcttcagc g    31

<210> SEQ ID NO 9
<211> LENGTH: 62
<212> TYPE: DNA
<213> ORGANISM: Artificial Sequence
<220> FEATURE:
<223> OTHER INFORMATION: primer

<400> SEQUENCE: 9
atacatatgc accatcatca tcatcatgac gacgacgaca aggcggggat gtcgctgacg    60
ca    62

<210> SEQ ID NO 10
<211> LENGTH: 36
<212> TYPE: DNA
<213> ORGANISM: Artificial Sequence
<220> FEATURE:
<223> OTHER INFORMATION: primer

<400> SEQUENCE: 10
gagctcgagt tatgactggg gtgcggcctt gatcag    36

<210> SEQ ID NO 11
<211> LENGTH: 63
<212> TYPE: DNA
<213> ORGANISM: Artificial Sequence
<220> FEATURE:
<223> OTHER INFORMATION: primer

<400> SEQUENCE: 11
atacatatgc accatcatca tcatcatgac gacgacgaca agcaggtggt taaggaaccg    60
gag    63

<210> SEQ ID NO 12
<211> LENGTH: 42
<212> TYPE: DNA
<213> ORGANISM: Artificial Sequence
<220> FEATURE:
<223> OTHER INFORMATION: primer

<400> SEQUENCE: 12
gagctcgagt tatttgtctt gcgagtcctt ttttattttg tc    42